United States Patent
Sahbaee Bagherzadeh et al.

(10) Patent No.: US 10,925,565 B2
(45) Date of Patent: Feb. 23, 2021

(54) MACHINE-LEARNING BASED CONTRAST AGENT ADMINISTRATION

(71) Applicant: Siemens Healthcare GmbH, Erlangen (DE)

(72) Inventors: Pooyan Sahbaee Bagherzadeh, Mount Pleasant, SC (US); Saikiran Rapaka, Pennington, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 302 days.

(21) Appl. No.: 15/950,430

(22) Filed: Apr. 11, 2018

(65) Prior Publication Data

US 2019/0313990 A1    Oct. 17, 2019

(51) Int. Cl.
| | |
|---|---|
| *A61B 6/00* | (2006.01) |
| *A61B 5/055* | (2006.01) |
| *A61B 5/00* | (2006.01) |
| *G06K 9/66* | (2006.01) |
| *G06N 3/08* | (2006.01) |
| *G06T 5/00* | (2006.01) |
| *G06F 30/20* | (2020.01) |

(52) U.S. Cl.
CPC .............. *A61B 6/481* (2013.01); *A61B 5/055* (2013.01); *A61B 5/7267* (2013.01); *A61B 6/583* (2013.01); *G06F 30/20* (2020.01); *G06K 9/66* (2013.01); *G06N 3/08* (2013.01); *G06T 5/009* (2013.01); *G06T 2207/10028* (2013.01); *G06T 2207/10072* (2013.01); *G06T 2207/20081* (2013.01); *G06T 2207/20084* (2013.01); *G06T 2207/30104* (2013.01)

(58) Field of Classification Search
None
See application file for complete search history.

(56) References Cited

U.S. PATENT DOCUMENTS

| | | | |
|---|---|---|---|
| 9,349,178 B1 | 5/2016 | Iru et al. | |
| 9,449,145 B2* | 9/2016 | Sankaran | ........... A61B 5/02007 |
| 2008/0027309 A1* | 1/2008 | Hempel | ................. A61B 6/481 |
| | | | 600/420 |
| 2013/0253314 A1 | 9/2013 | Kalafut et al. | |
| 2017/0258982 A1 | 9/2017 | Kemper | |
| 2018/0032841 A1 | 2/2018 | Kluckner et al. | |
| 2018/0071452 A1 | 3/2018 | Sharma et al. | |
| 2018/0184070 A1* | 6/2018 | Nash | ....................... G06T 7/593 |

(Continued)

OTHER PUBLICATIONS

Sahbaee, P. et al., "The Effect of Contrast Material on Radiation Dose at CT: Part I—Incorporation of Contrast Material Dynamics in Anthropomorphic Phantoms" Radiology, 2017, vol. 000, No. 0, pp. 1-9.

(Continued)

*Primary Examiner* — Kevin Ky

(57) ABSTRACT

A method comprises: inputting contrast enhancement data for at least one organ of a patient, at least one patient attribute of the patient, and a test bolus data or bolus tracking data to a regressor; receiving a contrast agent administration protocol from the regressor, based on the contrast enhancement data, the at least one patient attribute and the test bolus or bolus tracking data; and injecting a contrast agent into the patient according to the received contrast agent administration protocol.

21 Claims, 6 Drawing Sheets

(56) References Cited

U.S. PATENT DOCUMENTS

2019/0026466 A1* 1/2019 Krasser ............... G06N 3/0454

OTHER PUBLICATIONS

Sahbaee, P. et al., "The Effect of Contrast Material on Radiation Dose at CT: Part II—a Systematic Evaluation across 58 Patient Models" Radiology, 2017, vol. 000, No. 0, pp. 1-10.

Sahbaee, P. et al., "Determination of contrast media administration to achieve a targeted contrast enhancement in computed tomography" Journal of Medical Imaging, vol. 3(1), 013501(Jan.-Mar. 2016).

Konno, M. et al., "Cardiac output obtained from test bolus injections as a factor in contrast injection rate revision of following coronary CT angiography" Acta Radiologica, 2012; vol. 53, Issue 10, pp. 1107-1111.

Nijhof, W.H. et al., "A non-invasive cardiac output measurement as an alternative to the test bolus technique during CT angiography" Clinical Radiology, Sep. 2016, vol. 71, Issue 9, p. 940.e1-940.e5.

* cited by examiner

MACHINE-LEARNING BASED CONTRAST AGENT ADMINISTRATION

FIELD

This disclosure relates to medical imaging generally, and more specifically to contrast-enhanced imaging.

BACKGROUND

Dynamic contrast-enhanced (DCE) imaging provides dynamic information about the flow of an injected contrast agent through blood vessels to different tissues. Tissues with substantially different blood flow rates appear in a DCE image with contrasting tones. For example, DCE enables analysis of blood vessels generated by a brain tumor. The concentration of the contrast agent is measured as it passes from the blood vessels to the extracellular space of the tissue and as it goes back to the blood vessels, and magnetic resonance (MR) or computed tomography (CT) images are reconstructed from the concentration data.

The amount of contrast agent injected into the patient can be reduced for patient safety. A tradeoff can be made between reduction in the amount of contrast agent injected into the patient and contrast enhancement.

SUMMARY

In some embodiments, a method comprises inputting contrast enhancement data for at least one organ of a patient, at least one patient attribute of the patient, and a test bolus data or bolus tracking data to a regressor; receiving a contrast agent administration protocol from the regressor, based on the contrast enhancement data, the at least one patient attribute and the test bolus or bolus tracking data; and injecting a contrast agent into the patient according to the received contrast agent administration protocol.

In some embodiments, a system comprises a simulator for modeling flow of a contrast agent through a body and generating contrast enhancement data. A non-transitory, machine readable storage medium stores the contrast enhancement data, at least one patient attribute of a patient, and a test bolus or bolus tracking data of the patient. At least one processor includes a regressor configured to generate a contrast agent administration protocol, based on the contrast enhancement data and the at least one patient attribute.

In some embodiments, a non-transitory, machine-readable storage medium is encoded with instructions for controlling a processor, such that when the processor executes the instructions, the processor performs a method comprising: simulating flow of a contrast agent through a body and generating contrast enhancement data from the simulating; inputting at least one patient attribute of a patient to a regressor trained using the contrast enhancement data; and using the regressor to generate a scan delay between an injection of a contrast agent and a scan, such that performance of the scan after the injection and the scan delay captures an image of an organ with a peak contrast agent concentration in the organ.

DETAILED DESCRIPTION

This description of the exemplary embodiments is intended to be read in connection with the accompanying drawings, which are to be considered part of the entire written description.

This disclosure can provide fast, patient-specific estimation of an optimal contrast injection protocol, for organ-specific imaging applications. For a given amount of contrast agent (CA), the system and method can provide the greatest image contrast. Alternatively, for a given target contrast, the system and method can minimize the amount of contrast agent injected into the patient. The system can determine and implement an optimal, patient-specific contrast agent administration protocol and scan delay (i.e., delay between contrast agent injection and scanning) corresponding to the patient's cardiac output. The system and methods may lead to better image quality at significantly lower doses of contrast agent. The scan times can also be reduced significantly, while simultaneously maintaining high image quality.

Figure 1:
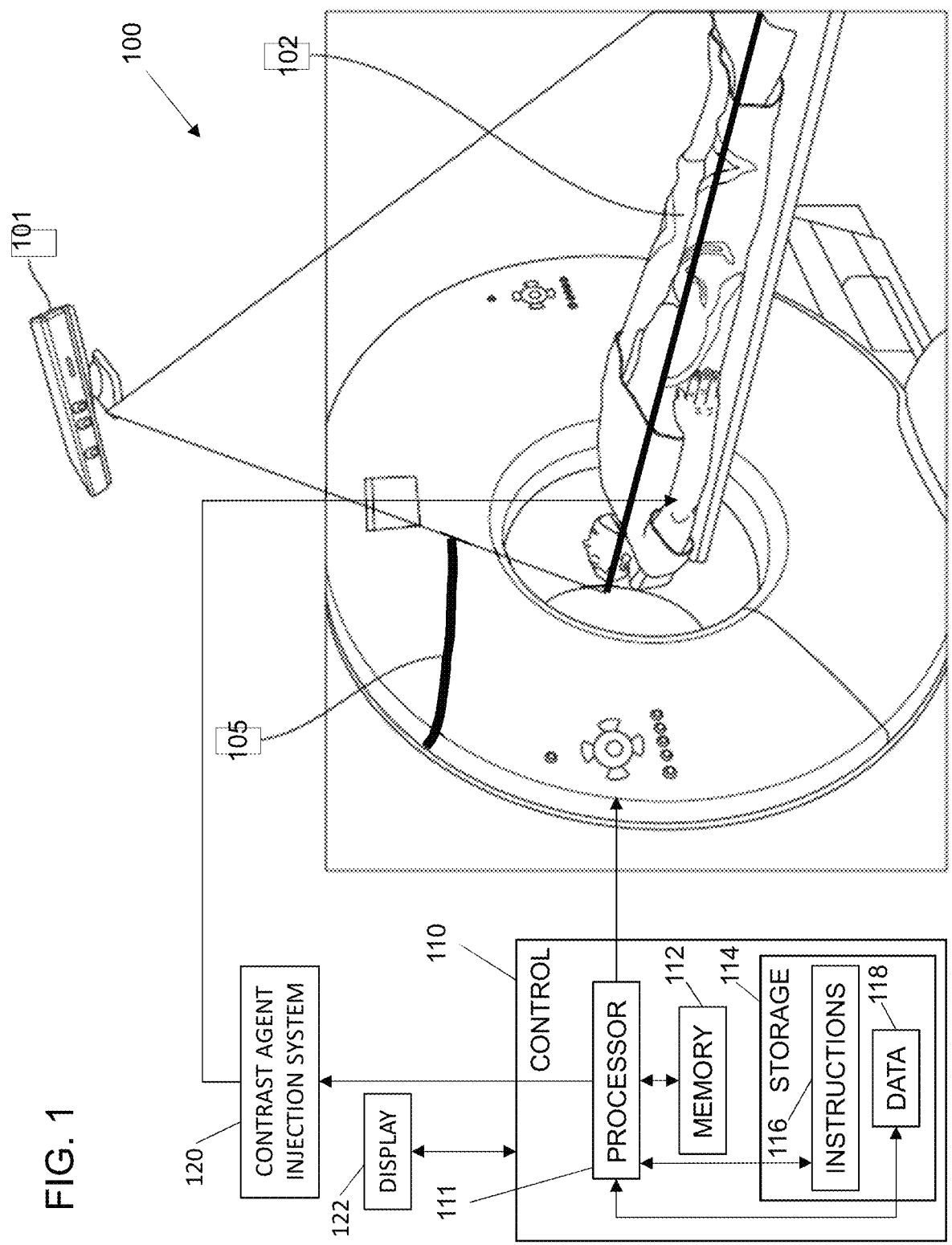
FIG. 1 is a schematic diagram of a system including machine-learning based contrast agent administration, according to an exemplary embodiment.

FIG. 1 shows a scanner system 100, including a control device 110 for controlling a scanner 105. The scanner 105 can be an magnetic resonance (MR) scanner, such as a "MAGNETOM VIDA"™ scanner, a computed tomography (CT) scanner, such as a "SOMATOM CONFIDENCE RT Pro"™ CT Scanner, a PET scanner, such as the "BIOGRAPH HORIZON"™ PET/CT scanner, or an ultrasound scanner, such as the "ACUSON SC2000PRIME"™ cardiovascular ultrasound system, all sold by Siemens Medical Solutions USA, Inc. of Malvern, Pa. The scanner can include an automated contrast agent injection system 120 automatic control of the injection profile, as provided by "CARE CONTRAST"™ in the "SOMATOM"™ scanner by Siemens Medical Solutions USA, Inc. of Malvern, Pa., where the contrast injector can be connected to the CT scanner, enabling synchronized injection and scanning.

The control device 110 has a processor 111 using machine learning to predict a scanning protocol for contrast enhancement imaging an internal organ (not shown) of the subject based on the prediction. The processor 111 is configured (e.g., by software) for controlling the scanner 105 based on the predicted contrast agent amount, injection profile, and delay between injecting the contrast agent and performing the scan. The processor 111 can issue commands to the automated contrast agent injection system 120, to inject a selected dosage of CA according to the predicted injection protocol. These are only examples, and other scanner makes and models may be used. The processor 111 can have user input/output devices, such as a display 122, which can be a touch-screen capable of receiving user inputs and displaying outputs. Other input devices (e.g., keyboard or pointing device, not shown) may be included.

The processor 111 can include an embedded processor, a computer, a microcontroller, an application specific integrated circuit (ASIC), a programmable gate array, or the like. The control device 110 includes a main memory 112, which can include a non-transitory, machine readable storage medium such as dynamic random access memory (DRAM). The secondary memory comprises a non-transitory, machine readable storage medium 114, such as a solid-state drive, hard disk drive (HDD) and/or removable storage drive, which can include a solid state memory, an optical disk drive, a flash drive, a magnetic tape drive, or the like. The non-transitory, machine readable storage medium 114 can include tangibly store therein computer software instructions 116 for causing the scanner 105 to perform various operations (described herein) and data 118.

The injection system 120 can perform calibrated injections to patients, starting from a multi-dose solution of iodine, fluorodeoxyglucose (FDG), or other radiopharmaceuticals. In some embodiments, the scanner 100 is not equipped with an automated injection system 120, in which case a separate injection system (not shown) may be used. For example, some systems can include an external injection system (not shown), such as the "IRIS™" Radiopharmaceutical Multidose Injector sold by Comecer S.p.A. of Castel Bolognese, Italy. In some embodiments, the injection system 120 has a wired or wireless communications link with the processor 111, for automatically transmitting dosage, contrast agent application protocol and scan delay to the injection system 120. In some embodiments, the processor 111 receives a value of a scan delay from a regressor (e.g., neural network) 220, to be used between an injection of the contrast agent and a scan from the neural network. The processor waits for approximately a period of time according to the scan delay after the injecting, and initiates performing a computed tomography scan or magnetic resonance scan (using the scanner) after the waiting. In some embodiments, the injection begins upon expiration of the scan delay. In other embodiments, the injection is timed so that the injection straddles the time of peak contrast agent concentration in the organ of interest, and the mid-point of the injection coincides with the time of peak contrast agent concentration.

The system 100 can include a two-dimensional (2D) or three-dimensional (3D) camera 101. In some embodiments, the 2D or 3D camera 101 captures an image of the patient before the scanning. The image can be used to estimate one or more patient attributes, such as patient height or weight, used by the control device 110.

Architecture for Model Acceleration

Figure 2:
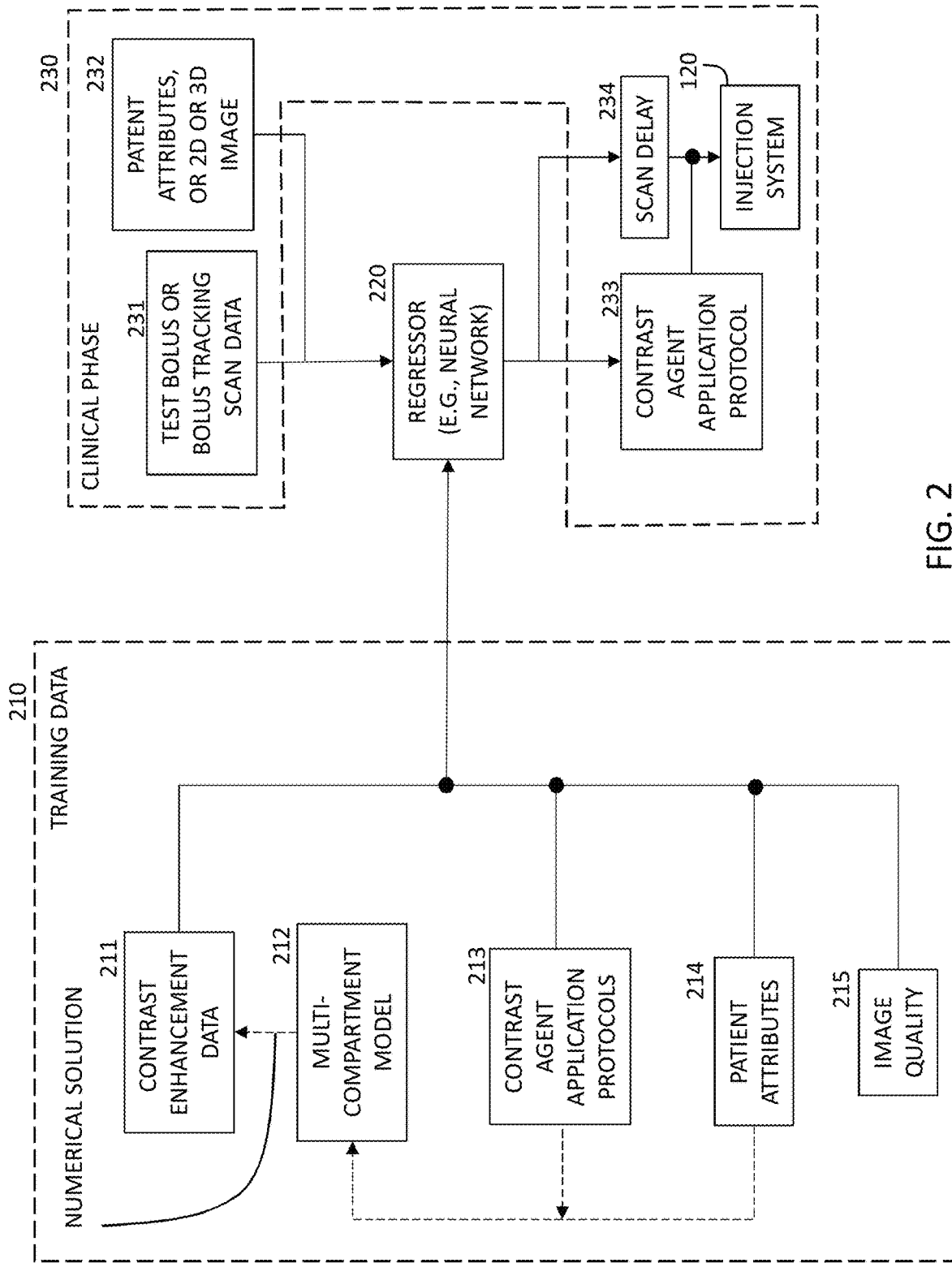
FIG. 2 is a block diagram of the system shown in FIG. 1.

FIG. 2 is a block diagram of a system for determining contrast agent application protocol and scan delay in real-time, based on a test bolus data or bolus tracking data, for immediate use in contrast enhanced scanning while the patient is still on the scanner bed.

Contrast agent uptake in the human body can be modeled using a simulator implementing a multi-compartment model 212 for modeling flow of a contrast agent through a body and generating contrast enhancement data. The contrast propagation through each compartment in the model 212 can be represented through a set of coupled differential equations, which can be solved to obtain the contrast agent concentration at any given location as a function of time. The results of the model 212 depend on the patient internal parameters, which can be personalized to the patient's attributes 214 (age, body mass, height, pathological condition, cardiac output, etc.). Once the model 212 is suitably parametrized, the model 212 can then be computationally "inverted". In some embodiments, this includes computing the initial contrast agent injection protocol that is used to obtain a desired contrast density curve at a given location. For instance, for scanning the liver, a desired contrast agent density curve at the liver can be input, and then the model can be inverted to compute the contrast agent administration protocol that should be followed, based on the contrast enhancement data and patient attributes.

Numerical solutions of the differential equations characterizing the multi-compartment models 212 may be computationally demanding and time consuming, but in some embodiments described herein, a trained regressor (e.g., neural network) 220 provides sufficient acceleration to determine the contrast agent application protocol 233 within the clinical workflow. In some embodiments, the neural network 220 is a deep neural network. In some embodiments, the neural network 220 is configured to perform support vector regression. For example, in some cases, the neural network 220 trained with contrast enhancement data 211 from the model 212 can generate a contrast agent administration protocol 223 about 80 times as fast as the numerical solution of the differential equations of the PBPK model 212. In the clinical phase, following the test bolus or bolus tracking scan 231, the trained neural network 220 can generate the contrast agent administration protocol 233 immediately, and the generated contrast agent administration protocol 233 can be implemented while the patient is still on the scanner bed.

Combining machine learning techniques with physiological based compartmental modeling and real-time test bolus or bolus tracking curves 231 from the scanner 100, the regressor (e.g., neural network) 220 can generate the contrast agent application protocol 233 and scan delay 234 parameters corresponding to the desired contrast enhancement in any targeted organ or blood vessel.

The personalized model parameters 211, 213, 214, 215 from the offline numerical solution stage become training input parameters to the contrast propagation regressor (e.g., neural network) 220. This regressor (e.g., neural network) 220 evaluates the contrast enhancement data 211 defining the relationship between the injected contrast volume and its distribution at different locations as a function of time. Then, given the organ (or region) of interest to be imaged, an optimal contrast agent application protocol 233 (including a CA injection curve) is selected based on the patient-specific model parameters 232.

One approach to achieve significant acceleration of determining the CA administration protocol 233 and scan delay 234 is through the use of machine learning algorithms. In this approach, the regressor (e.g., neural network) 220 learns the relationship between the inputs (CA administration curve of test bolus data or bolus tracking data 231 and patient attribute, such as 2D or 3D image 232 from camera 101) and the outputs (resulting contrast agent application protocol 233 and scan delay 234). A large database 210 of the inputs (multi-compartment model 212, contrast agent application protocols 213, patient attributes 214 and, in some embodiments, image quality 215) and outputs (contrast enhancement data 211, also referred to herein as "synthetic data") is used to train a machine learning system (regressor 220). The regressor 220 learns to determine the relationship between the inputs and outputs, to determine an optimum contrast agent application protocol 233 and scan delay 234 given the test bolus data or bolus tracking data 231 and 2D or 3D image 232 from camera 101.

In some embodiments, the regressor 220 is a deep neural network having a plurality of coefficients. The coefficients are machine-learned by inputting a plurality of patient parameters (attributes) 214 and a plurality of contrast agent injection protocols 213 to a simulator 212, simulating flow of a contrast agent through a plurality of patients' bodies using the simulator 212, and providing the contrast enhancement data 211 based on the simulating, for use in the neural network.

In various embodiments, the following different approaches can be used to generate the database:

1) The training data 210 can be generated by multiple runs of numerically solving the differential equations of the multi-compartment model 212, using different sampling methods to generate random inputs, model parameters and the corresponding outputs. The different model parameters can be sampled (e.g., using different random number generators, or using other sampling methods) to span the range of physiological interest.

(2) Data acquired using controlled experiments on phantom datasets, where organs with different properties are prepared and imaged.

(3) Actual medical images acquired from past patients.

A large training dataset 210 is used to cover the domain of patient attributes. The available medical image data sets from past patients may not be large enough to train the regressor 220. According to some embodiments, any combination of data obtained by methods (1) to (3) can be used to provide enough training data.

In some embodiments, the regressor 220 can include multiple models, each looking at the input-output relationship for a specific blood vessel compartment or organ. One example is the machine learning based fractional flow reserve (FFR) prediction model, which has shown high accuracy compared to the numerical solution of the differential equations of the underlying physics model, while providing an 80-fold acceleration in the computational runtime.

The machine learning model in regressor 220 can also take account of any constraints the injection system may impose on the contrast agent application protocol 233. For instance, the regressor 220 can accommodate limits placed on the peak injection rate, total volume injected, smoothness of the injection curve etc. For instance, if a constant injection rate is desired, the regressor 220 can produce a specific injection rate which would minimize the contrast agent volume, to get as close as possible to the desired contrast distribution at the target organ.

Model Personalization

The system in FIG. 2 provides model personalization using a data-driven approach. The patient attributes 214 and contrast agent administration protocols 213 are input to the multi-compartment model 212, which numerically solves the differential equations to generate contrast enhancement data 211, as indicated by dashed arrows.

During the model personalization, each image (of previous patients) can be augmented with a quantitative "image quality" metric 215. The operator can input a quality metric based on the image obtained from a computed tomography scan or magnetic resonance scan. The image quality metric 215 can either be computed algorithmically based on different image features (for instance, contrast), or annotated by a clinical team, or a combination of both. The contrast enhancement data 211, contrast agent application protocol 213, patient attributes 214, and in some cases, image quality 215 can then form the training dataset 210 to input to the regressor 220. The regressor 220 takes into account the combination of different patient attributes 214 (e.g., either input or estimated from 2D or 3D image 232 from camera 101), along with the image quality 215 (if available), contrast enhancement data 211, scan delay (i.e., time difference between injection and image acquisition) and other features from the test bolus data or bolus tracking data 231 to learn a functional mapping between the features from the test bolus or bolus tracking scan image 231 and contrast agent application protocol 233 and scan delay 234 providing the optimal image quality. The operator can use the machine learning to reduce the contrast agent amount of a subsequent computed tomography scan or magnetic resonance scan or increase an image contrast of the subsequent computed tomography scan or magnetic resonance scan based on the quality metric.

For each organ of each patient, the training data 210 can include the contrast enhancement data 211 (obtained from the multi-compartment model 212), contrast agent application protocol 213, patient attributes 214, and in some cases, image quality 215. Once trained based on the database 210 of past patient image acquisitions and/or phantom data and/or synthetic data covering a wide range of patient attributes 214, regressor 220 can provide patient-specific contrast agent application protocol 233 and scan delay 234 for any given test bolus data or bolus tracking data 231 and patient attributes or 2D or 3D image 232.

One of the challenges in modeling the accurate patient-specific contrast agent distribution in individual patients is the estimation of cardiac output in real time. During the clinical phase 230, cardiac output can be estimated from a test bolus data or bolus tracking data 231, which can be input to regressor 220. Information acquired from the test bolus data or bolus tracking data 231 with additional patient attributes or 2D or 3D image data 232 for all the organs and vessels can enhance accuracy. Once the regressor 220 is trained, the regressor 220 can be applied to a test bolus data or bolus tracking data 231 of a new patient. The test bolus data or bolus tracking data 231 can be performed with a low dose injection of the contrast agent. In some embodiments, for each clinical phase patient, the information from the test bolus data or bolus tracking data 231 is combined with patient attributes 232 (which can be input directly or estimated based on a 2D or 3D image from camera 101) and input to the regressor 220 to find a contrast agent application protocol 233 and scan delay 234 to optimize the correlation between the contrast intensity at a given location and the patient attributes 214 during an imaging scan.

Patient attributes (e.g., height, weight) 232 can be input directly, or in some embodiments, a 2D or 3D image of the patient (indicative of one or more attributes of the patient) is also captured using a digital camera 101. The input patient parameters 232 can be estimated based on the 2D or 3D image. The network or regressor 220 then uses input patient attributes 232, along with a set of features computed on the test bolus data or bolus tracking data 231 to infer the patient-specific model parameters (e.g., the contrast agent application protocol 233 and scan delay 234).

In some embodiments, a 3D avatar mesh of the subject is formed based on a 2.5D or 3D image from the camera 101, as disclosed in US 2015/0213646 A1 (application Ser. No. 14/604,829, filed Jan. 26, 2015), which is incorporated by reference herein in its entirety. The height or other spatial attribute of the patient can be determined from the 3D avatar mesh. For example, in some embodiments, a depth camera image of the subject is converted to a 3D point cloud. A plurality of anatomical landmarks are detected in the 3D point cloud. A 3D avatar mesh is initialized by aligning a template mesh to the 3D point cloud based on the detected anatomical landmarks. A personalized 3D avatar mesh of the subject is then generated by optimizing the 3D avatar mesh using a trained parametric deformable model (PDM).

Model-Based Contrast Administration Protocol

A physiologically based pharmacokinetic (PBPK) model 212 can simulate contrast agent propagation in the human body. Simplified effective models are provided for each organ, parametrized by a reduced set of parameters to address the forward model of contrast propagation, given the initial injection curve. An exemplary systems model is shown in FIG. 3.

In some embodiments, model-based optimization can be used for selecting the contrast agent injection protocols. For example, FIG. 3 shows an example of a multi-compartment model for blood and contrast agent flow through the body. FIG. 3 is a sample schematic diagram of a physiologically based pharmacokinetic (PBPK) model of a human body. The model can predict absorption, distribution, and metabolism of the contrast agent within the body, beginning with injection. In FIG. 3, each block (3, 8, 11, 14, 16, 20, 21, 23, 25, 28, 29, 32 and 36) represents an organ compartment, and each ellipse (1, 2, 4-7, 9-10, 12, 13, 15, 17-19, 22, 24, 26, 27, 30-31, 33-35, and 37) represents a blood vessel compartment.

Figure 3:
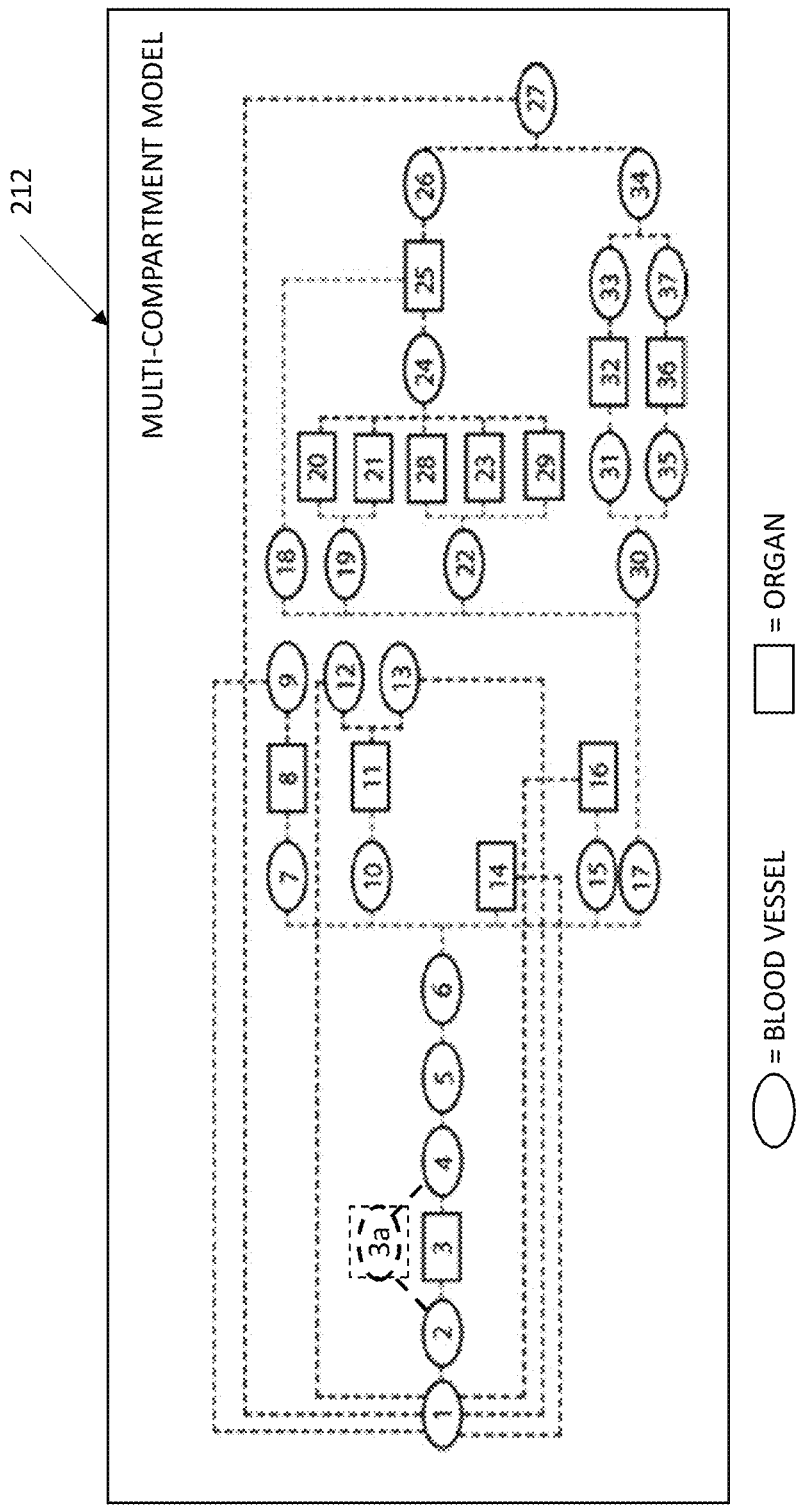
FIG. 3 is a schematic diagram of the multi-compartment model of FIG. 2.

Table 1 lists the compartments of the model of FIG. 3 and their respective descriptions, according to one example. The compartments in Table 1 are numbered in the order in which they appear in FIG. 3. In the compartmental model of Table 1 and FIG. 3, the heart is represented by three separate compartments: the left heart, right heart, and heart muscle. Because of the negligible amount of perfusion occurring in left and right heart, they are assumed to be vessel compartments. Table 1 only includes the organs' names (except aorta), and the vessels are named with their compartment numbers (except aorta). Although the nodes of the model begin with the right heart (compartment No. 1), the injection can be performed at any injection site (compartment), and the contrast agent flows to the remaining compartments in the order listed, and after the iliac vein (compartment No. 37) flows the right heart (compartment No. 1) and continues in order.

TABLE 1

Estimated Blood Distribution in the Vascular System, Blood Flow Rate, and Capillary Volumes Used in PBPK Model

| Compartment | Type | Blood Flow Rate (mL/sec) | Intravascular Volume (mL) | Extra-cellular Volume (mL) |
|---|---|---|---|---|
| 1. Right heart | Vessel | 29.0 | 180 | 0 |
| 2. Pulmonary artery | Vessel | 108.3 | 130 | 0 |
| 3. Lung parenchyma | Organ | 108.3 | 150 | 144 |
| 4. Pulmonary vein | Vessel | 108.3 | 160 | 0 |
| 5. Left heart | Vessel | 108.3 | 180 | 0 |
| 6. Aorta | Vessel | 108.3 | 100 | 0 |
| 7. Carotid artery | Vessel | 16.3 | 20 | 0 |
| 8. Head | Organ | 16.3 | 37 | 484 |
| 9. Superior jugular vein | Vessel | 16.3 | 80 | 0 |
| 10. Subclavian aorta | Vessel | 5.4 | 20 | 0 |
| 11. Upper extremity | Organ | 5.4 | 12 | 2751 |
| 12. Superior vena cava | Vessel | 2.7 | 40 | 0 |
| 13. Superior vena cava | Vessel | 2.7 | 40 | 0 |
| 14. Heart muscle | Organ | 4.3 | 10 | 103 |
| 15. Bronchial artery | Vessel | 82.3 | 100 | 0 |
| 16. Lung nonparenchyma | Organ | 2.2 | 5 | 144 |
| 17. Descending aorta | Vessel | 80.2 | 100 | 0 |
| 18. Hepatic artery | Vessel | 7.5 | 20 | 0 |
| 19. Mesenteric artery | Vessel | 15.5 | 20 | 0 |
| 20. Small intestine | Organ | 15.6 | 20 | 322 |
| 21. Colon | Organ | 15.6 | 14 | 218 |
| 22. Celiac artery | Vessel | 8.2 | 20 | 0 |

TABLE 1-continued

Estimated Blood Distribution in the Vascular System, Blood Flow Rate, and Capillary Volumes Used in PBPK Model

| Compartment | Type | Blood Flow Rate (mL/sec) | Intravascular Volume (mL) | Extra-cellular Volume (mL) |
|---|---|---|---|---|
| 23. Stomach | Organ | 8.25 | 10 | 62 |
| 24. Portal vein | Vessel | 23.8 | 100 | 0 |
| 25. Liver | Organ | 7.5 | 71 | 524 |
| 26. Renal vein | Vessel | 31.4 | 100 | 0 |
| 27. Inferior vena cava | Vessel | 80.1 | 800 | 0 |
| 28. Pancreas | Organ | 8.25 | 2 | 12 |
| 29. Spleen | Organ | 8.25 | 6 | 37 |
| 30. Abdominal aorta | Vessel | 48.7 | 80 | 0 |
| 31. Renal artery | Vessel | 23.8 | 20 | 0 |
| 32. Kidney | Organ | 23.8 | 54 | 89 |
| 33. Renal vein | Vessel | 23.8 | 100 | 0 |
| 34. Inferior vena cava | Vessel | 48.7 | 700 | 0 |
| 35. Iliac artery | Vessel | 24.9 | 200 | 0 |
| 36. Trunk and lower extremities | Organ | 24.9 | 57 | 11002 |
| 37. Iliac vein | Vessel | 24.9 | 1000 | 0 |

The flows of contrast agent into and out of each organ, and changes in concentration within the organ, can be expressed by a respective differential equation. For example, the differential equations for each organ can indicate that blood flow rate out of the organ equals blood flow rate into the organ, while the rate of change in CA concentration in the organ varies with the blood flow rate through the organ and the difference between the input CA concentration and the output CA concentration. This set of differential equations is described in Sahbaee, Pooyan, et al. "The effect of contrast agent on radiation dose at CT: part I. Incorporation of contrast agent dynamics in anthropomorphic phantoms." Radiology 283.3 (2017): 739-748, which is incorporated by reference herein. The set of differential equations can be solved numerically, to predict absorption, distribution and metabolism. Numerical solutions for a large PBPK model, such as model 212, may be computationally expensive. For example, the contrast agent flow in the model of FIG. 3 is described by approximately 300 differential equations.

The computational models based on the solution of large sets of coupled differential equations have a long computational time. In some embodiments, the differential equations for the model 212 are solved many (e.g., 10,000) times over the domain of contrast agent administration protocols 213 and patient attributes 214, to generate a large set of contrast enhancement data 211. This dataset 210 can be generated a single time, prior to training. Once the regressor 220 is trained, the regressor 220 can generate contrast agent administration protocols 233 and scan delay 234 in real time during patient contrast enhanced image scanning.

The 37-compartment model of FIG. 3 is just an example. Any multi-compartmented model can be used, in accordance with the desired accuracy and/or desired computation time and complexity. For example, the model of FIG. 3 includes a single compartment for the small intestine and a single compartment for the large intestine. In other embodiments, the small intestine and/or large intestine could be modeled as two or more compartments. Further, the disclosed system can be applied for any organs with more than one input "vessel" (e.g., liver) and/or for any organ having more than one output vessel.

Figure 4:
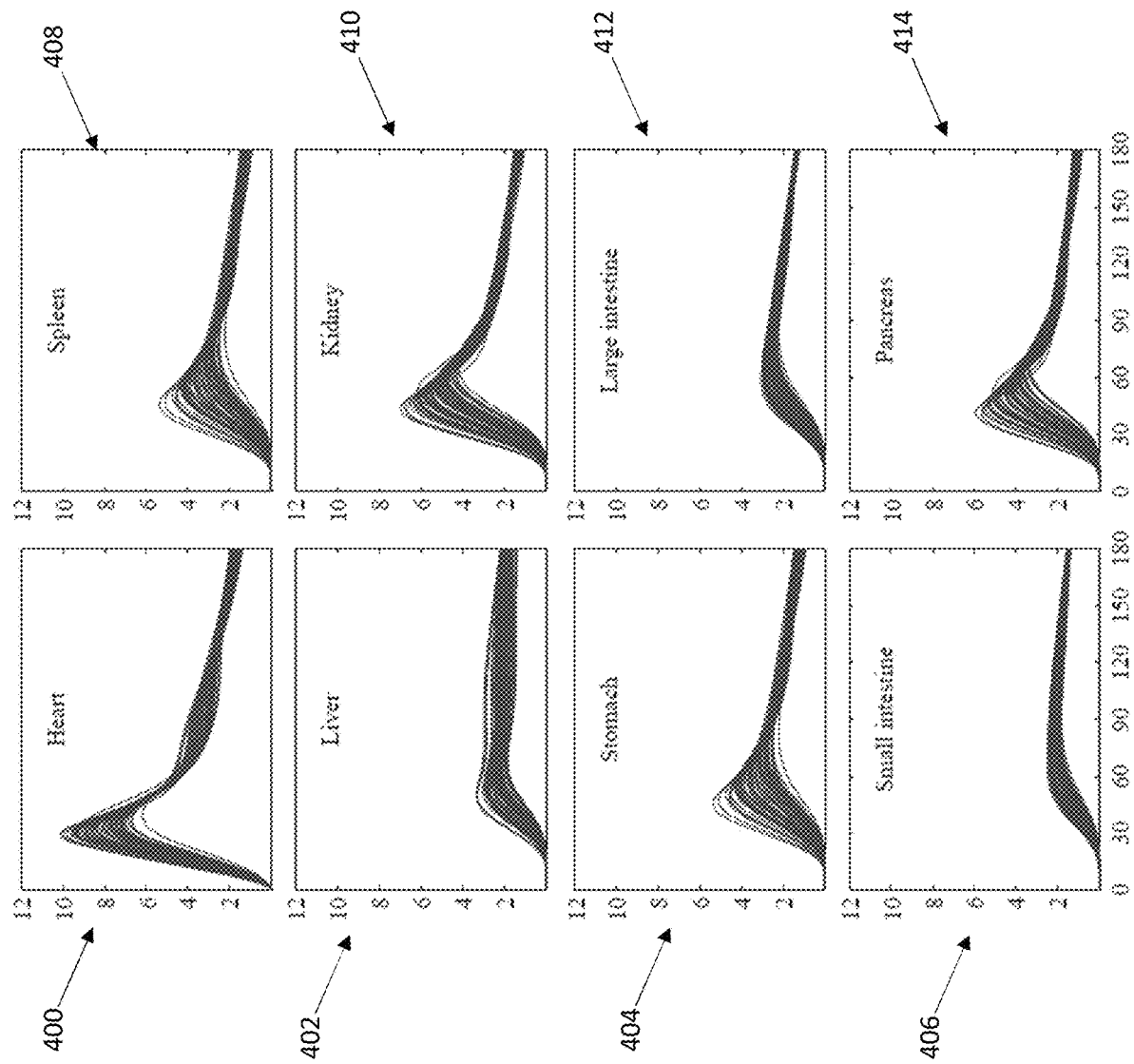
FIG. 4 shows contrast enhancement data provided by the multi-compartment model of FIG. 3.

For example, FIG. 4 shows sets of contrast enhancement data 211 generated by the multi-compartmented model 212. Separate contrast enhancement data are provided for each organ. For example, the data include several contrast enhancement curves for each of: heart 400, liver 402, stomach 404, small intestine 406, spleen 408, kidney 410, large intestine 412, and pancreas 414. The various curves for each organ correspond to different inputs (e.g., contrast agent application protocols 213 and/or patient attributes 214).

In some embodiments, to more accurately model the contrast enhancement curves in both healthy organs and in organs with pathology, the model can further include one or more lesion compartments connected to one or more organs and/or blood vessels. A model including a separate lesion compartment can be more realistically representative of patients. For example, referring again to FIG. 3, a lesion compartment 3a may be added to represent a tumor on a patient's lung.

Figure 5:
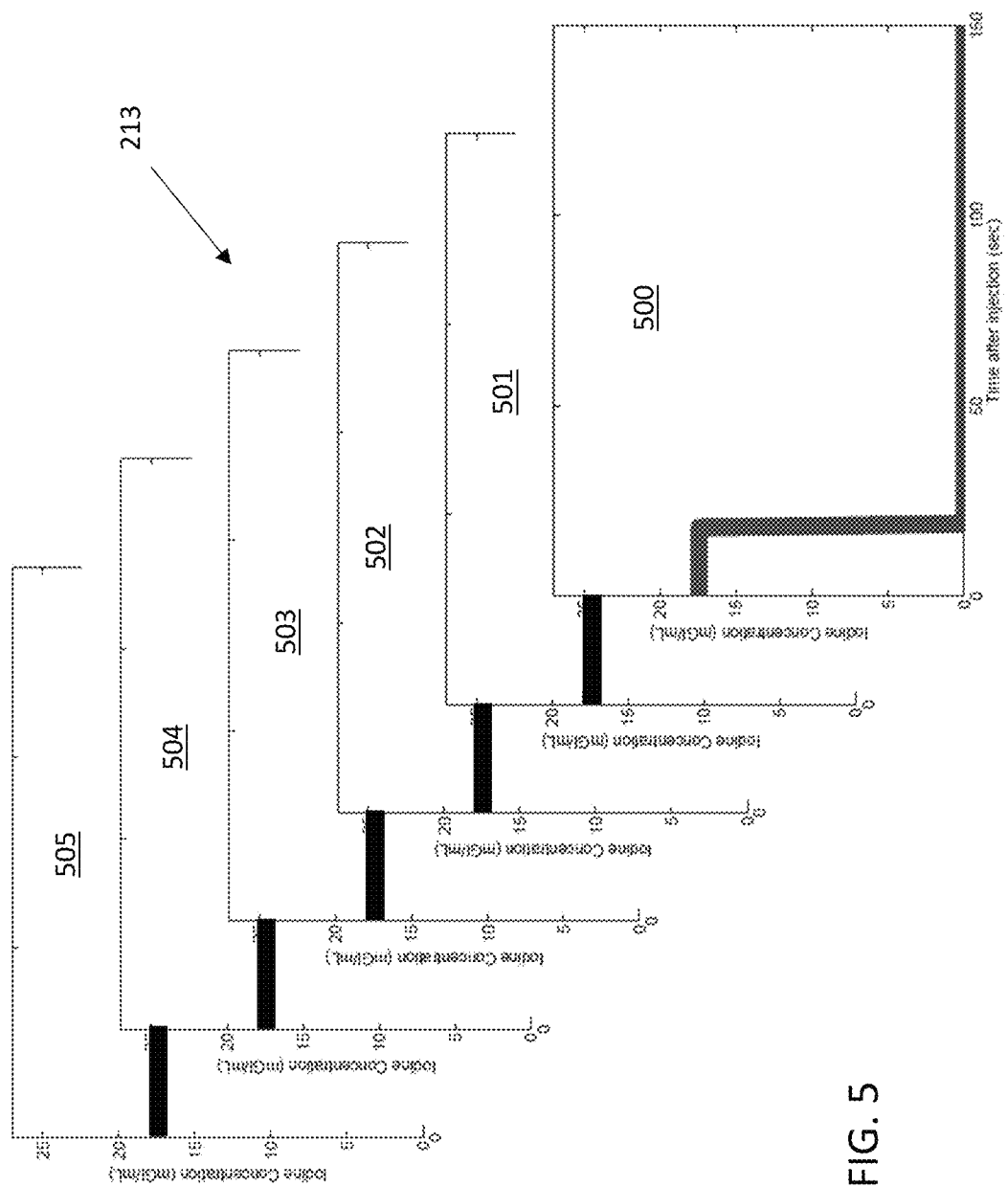
FIG. 5 shows contrast agent administration protocols input to the multi-compartment model of FIG. 2.

The training dataset 210 also includes a plurality of different contrast agent administration protocols 213. FIG. 5 shows an example of a set 213 of contrast agent administration protocols 500-505. Each contrast agent administration protocols (e.g., 500) has a respectively different amount of contrast agent (e.g., iodine) injected per unit of time, as a function of time during injection. In the exemplary contrast agent administration protocols 213 of FIG. 5, the contrast agent is injected at a constant rate for a first period, and then the injection stops. In other embodiments, the amount of contrast agent injected per unit of time can vary. For example, the amount of contrast agent injected per unit of time can ramp up during a first period, remain constant during a second period, ramp down during a third period, and then remain at zero. This is only an example, and other injection profiles can be used.

Some embodiments of this disclosure use a machine-learning-based framework of high computational efficiency. A neural network can be trained using "synthetic data" generated by numerical solution of the multi-compartment model. The training set includes a diverse group (e.g., 10,000) of patient examples covering the domain of patient characteristics (age, sex, weight, height, etc.) and contrast agent administration protocols. The synthetic data may be supplemented with clinical patient data and/or phantom data (e.g., XCAT phantom data) to ensure that the training set is sufficiently large. Once the neural network is trained, an application can use the neural network to generate imaging protocol parameters (contrast agent dosage, injection profile, and delay between injection and scan) in real-time conditions, enabling simple user workflows. A real-time test bolus or bolus tracking scan is performed using a low dosage of a contrast agent (CA), and a test bolus enhancement curve is generated. The test bolus enhancement curve from test bolus or bolus tracking scan 231 and the patient attributes or 2D or 3D image 232 are then input to the neural network 220, which generates the parameters of the contrast agent administration protocol 233 and the scan delay 234. The resulting imaging protocol maximizes contrast with a minimum contrast agent amount.

The synthetic data generated by the multi-compartment PBPK model 212 can be used to feed and train a deep learning network or regressor 220 to predict the contrast agent injection function for a desired enhancement in different organs. The PBPK model can provide any desired number of contrast enhancement perfusion data as function of time, throughout the domain of patient characteristics, for training the contrast-enhancement prediction machine learning network.

Optimization of CA administration protocol 233 properly orchestrated with the scan parameters (e.g., scan timing) enhances medical imaging, maintains high image quality, for any medical scanner technology using contrast enhancement in clinical practice. Because the regressor 220 is trained using samples throughout the domain of patient types (patient size, body mass index, etc.) the acquired images are of consistent quality regardless of patient characteristics. This also supports any downstream applications which use the medical images. For instance, in the cardiac use case, consistent gray values across patients will enable much more accurate determination of coronary centerline, and enable more accurate lumen segmentation.

Figure 6:
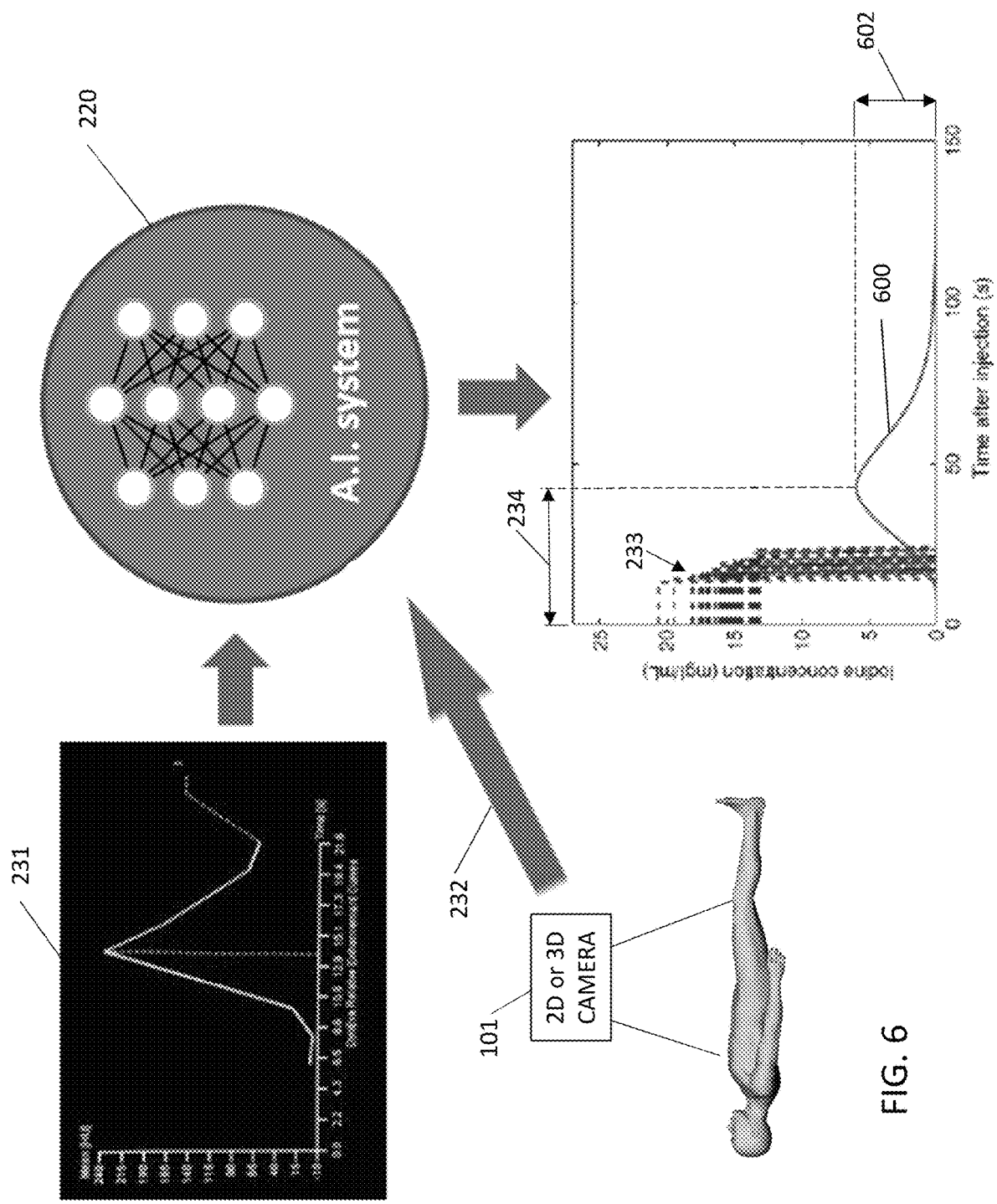
FIG. 6 is an information flow diagram for the system of FIG. 1.

FIG. 6 is a schematic diagram of the system in its configuration for clinical use. The trained regressor 220 (e.g., neural network) receives the real time test bolus or bolus tracking data 231 and a 2D or 3D image 232 from camera 101 as the inputs. The regressor 220 uses these inputs to accurately predict the cardiac output for individual patients, and consequently provide more precise individual contrast enhancement curves in different organs. For example, as shown in FIG. 6, the regressor 220 can provide respective contrast injection curves 233 (contrast agent application protocol) for the heart, spleen, liver, kidney, stomach, large intestine, small intestine, and pancreas. The regressor 220 also provides a contrast enhancement curve 600, from which the maximum contrast agent concentration 602 and the scan delay 234 corresponding to the maximum concentration value 602 can be determined. These outputs are then used immediately for contrast imaging while the patient is still on the bed. The quantity of contrast agent, contrast agent administration protocol, and the scan delay (relative to the beginning of injection) are based on the outputs of the regressor 220.

Because the PBPK model 212 is used during training (but not during real-time clinical use), the computation time of solving the differential equations of the PBPK model 212 does not pose an impediment to patient-specific scan protocol generation using the regressor 220. Using the previously trained regressor 220 and fine-tuning the different patient-specific parameters 232 (e.g., cardiac output, age, sex, organ and vessel sizes), injection protocol parameters (e.g., iodine concentration, volume, and injection rate) 233 and scan delay 234, the system can collect numerous contrast enhancement data in different organs.

Additionally, although the inputs to the PBPK model 212 are patient specific, they are independent of the neural network 220 and independent of the imaging scanner make and model. Once a training set 210 including synthetic data from the PBPK model 212 is generated, the same training set 210 can be used to determine the injection protocol for any scanner. Also, the same training set can be used to train a variety of machine learning systems (e.g., a variety of deep neural networks) to generate the injection protocols.

Modes of User-Interaction

The network or regressor 220 can be used in a variety of embodiments. For example, In some embodiments, the system includes a non-transitory machine readable storage medium 114 containing a plurality of different "desired contrast distributions" for each organ. The system can include a regressor 220 configured for receiving the test bolus or bolus tracking enhancement curve 231 and fetching the desired contrast distribution (FIG. 4) corresponding to the organ of interest, and generating a respective contrast agent administration protocol (e.g., injection function).

In some embodiments, the processor 111 system can provide touch-based interfaces for displaying data and prompts, and for receiving user inputs. For example, a touch screen display 122 (FIG. 1) can be used to display prompts to instruct the user for clicking on the organ of interest, either in a simple anatomical map, or on the organ of interest on the test bolus or bolus tracking scan 231. In some embodiments, the system can provide voice-activated or natural language interfaces, so the operator can speak voice commands to instruct the system (e.g., to acquire a coronary image).

In some embodiments, the system prompts the operator for approval of an estimate of the dose and the generated injection curve, before automatically commencing injection.

In some embodiments, the system 100 is configured to receive an operator input rating the quality of each scan upon completion. The system 100 is configured to incorporate the rating data for continuously learning the best injection protocols to minimize dose and contrast volume, while maximizing image quality. The learning machine of regressor 220 can learn from the difference between the prediction results and real data.

In some embodiments, the system 100 is configured to prompt the operator to select from one or more past cases in which the output image contrast was high. The network or regressor 220 calibrates or adapts itself to new patients based on the selected past case(s), to obtain images having similar quality or better quality.

In some embodiments, a summary of the machine learning from a plurality of scanner systems can be collected periodically and used to identify best practices, which can be disseminated to improve network or regressor 220 performance over the installed fleet of scanners.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method comprising:
    inputting contrast enhancement data for at least one organ of a patient, at least one patient attribute of the patient, and a test bolus data or bolus tracking data to a regressor, wherein the regressor is trained on a contrast enhancement data set generated by modeling a flow of a contrast agent through a body;
    receiving a contrast agent administration protocol from the regressor, based on the contrast enhancement data, the at least one patient attribute and the test bolus or bolus tracking data; and
    injecting a contrast agent into the patient according to the received contrast agent administration protocol, wherein the regressor is trained by:
        inputting a plurality of patient parameters and a plurality of injection protocols to a simulator;
        simulating flow of a contrast agent through a plurality of patients' bodies using the simulator; and
        providing a plurality of contrast enhancement data based on the simulating.

2. The method of claim 1, wherein the contrast agent administration protocol includes at least one a contrast agent amount and a contrast agent injection function.

3. The method of claim 2, further comprising:
    receiving a value of a scan delay between an injection of the contrast agent and a scan;
    waiting for at least a period of time according to the scan delay after the injecting; and
    performing a computed tomography scan or magnetic resonance scan after the waiting.

4. The method of claim 3, further comprising
    inputting a quality metric based on the computed tomography scan or magnetic resonance scan, and
    using machine learning to reduce the contrast agent amount of a subsequent computed tomography scan or magnetic resonance scan or increase an image contrast of the subsequent computed tomography scan or magnetic resonance scan based on the quality metric.

5. The method of claim 2, wherein the contrast agent injection function includes a respective contrast agent injection function for each of a plurality of organs.

6. The method of claim 1, wherein the regressor performs support vector regression.

7. The method of claim 1, further comprising providing additional contrast enhancement data based on measured patient data or phantom data.

8. The method of claim 1, wherein the simulator has a multi-compartment model relating the contrast agent amount and a distribution of the contrast agent at a plurality of different locations within a body of the patient as a function of time.

9. The method of claim 8, wherein the multi-compartment model has respective compartments for at least one organ and at least one blood vessel of the patient.

10. The method of claim 9, wherein the multi-compartment model further comprises a compartment corresponding to a lesion.

11. The method of claim 1, wherein the contrast agent injection function is selected from a plurality of previously stored contrast distributions for each of a plurality of organs.

12. The method of claim 1, wherein the patient attribute includes at least one of a patient weight, a patient surface area, a patient age, a patient height or a marker.

13. The method of claim 1, further comprising:
    capturing a depth image of the patient; and
    estimating the patient attribute based on the depth image and based on a computational phantom or a database containing previously collected patient data.

14. The method of claim 1, wherein the method further comprises additional training of the regressor using at least one of functional test data or phantom data.

15. A system comprising:
    a simulator for modeling flow of a contrast agent through a body and generating contrast enhancement data;

a non-transitory, machine readable storage medium storing the contrast enhancement data for at least one organ of a patient, at least one patient attribute of the patient, and a test bolus or bolus tracking data of the patient; and at least one processor including a regressor configured to generate a contrast agent administration protocol, based on the contrast enhancement data set generated by modeling a flow of a contrast agent through a body and the at least one patient attribute, wherein the regressor is trained by:
inputting a plurality of patient parameters and a plurality of injection protocols to a simulator;
simulating flow of a contrast agent through a plurality of patients' bodies using the simulator; and
providing a plurality of contrast enhancement data based on the simulating.

16. The system of claim 15, wherein the regressor includes a neural network.

17. The system of claim 15, wherein the simulator has a multi-compartment model relating the contrast agent amount and a distribution of the contrast agent at a plurality of different locations within the patient as a function of time.

18. The system of claim 17, wherein the multi-compartment model has respective compartments for at least one organ and at least one blood vessel of the patient.

19. The system of claim 15, wherein the regressor is further configured to generate a value of a scan delay between an injection of the contrast agent in the patient and a scan, and the system further comprises a computed tomography scanner or a magnetic resonance scanner for capturing the test bolus data or bolus tracking data and for capturing medical image data with the injection of the contrast agent and a scan separated by the scan delay.

20. The system of claim 15, wherein the regressor performs support vector regression.

21. A non-transitory, machine-readable storage medium encoded with instructions for controlling a processor, such that when the processor executes the instructions, the processor performs a method comprising:
inputting contrast enhancement data for at least one organ of a patient, at least one patient attribute of the patient, and a test bolus data or bolus tracking data to a regressor, wherein the regressor is trained by:
inputting a plurality of patient parameters and a plurality of injection protocols to a simulator;
simulating flow of a contrast agent through a plurality of patients' bodies using the simulator; and
providing a plurality of contrast enhancement data based on the simulating;
receiving a contrast agent administration protocol from the regressor, based on the contrast enhancement data, the at least one patient attribute and the test bolus or bolus tracking data; and
using the regressor to generate a scan delay between an injection of a contrast agent to the patient and a scan, such that performance of the scan after the injection and the scan delay captures an image of the at least one organ of the patient with a peak contrast agent concentration in the organ.

* * * * *